United States Patent [19]
Haddad et al.

[11] Patent Number: 4,933,312
[45] Date of Patent: Jun. 12, 1990

[54] MALEIC ANHYDRIDE CATALYSTS AND PROCESS FOR THEIR MANUFACTURE

[75] Inventors: Muin S. Haddad, Naperville; Bernard L. Meyers, Wheaton; William S. Eryman, Naperville, all of Ill.

[73] Assignee: Amoco Corporation, Chicago, Ill.

[21] Appl. No.: 297,329

[22] Filed: Jan. 17, 1989

[51] Int. Cl.$^5$ ............................................ B01J 27/198
[52] U.S. Cl. ..................................................... 502/209
[58] Field of Search ........................................ 502/209

[56] References Cited
U.S. PATENT DOCUMENTS

| | | | |
|---|---|---|---|
| 3,977,998 | 8/1976 | Freerks et al. | 502/209 |
| 4,396,535 | 8/1983 | Bremer et al. | 502/209 X |
| 4,699,895 | 10/1987 | Edwards | 502/209 |

*Primary Examiner*—W. J. Shine
*Attorney, Agent, or Firm*—Gunar J. Blumberg; William H. Magidson; Ralph C. Medhurst

[57] ABSTRACT

Novel maleic anhydride catalysts comprising phosphorus-vanadium oxides and phosphorus-vanadium-co-metal oxides which under reaction conditions for the manufacture of maleic anhydride from butane feedstock do not expand.

24 Claims, No Drawings

MALEIC ANHYDRIDE CATALYSTS AND PROCESS FOR THEIR MANUFACTURE

FIELD OF THE INVENTION

The field of this invention relates to novel catalysts and to processes for the manufacture of phosphorus-vanadium mixed oxide and phosphorus-vanadium-co-metal mixed oxide catalysts suitable for the oxidation of benzene, butane, butene, and butadiene to maleic anhydride wherein under oxidation conditions of the hydrocarbon the catalyst particles do not expand.

BACKGROUND

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs.

In general, catalysts proposed for the oxidation of butane to maleic anhydride have been based upon vanadium and phosphorus. In U.S. Pat. No. 3,293,268, it is disclosed that the oxidation of butane to maleic anhydride can be performed in the presence of a phosphorus-vanadium-oxygen-containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339; 4,403,943; 4,154,703 and British Application No. 2,019,839A. While the aforementioned prior art tends to bring about some improvement in the performance of the phosphorus-vanadium catalyst, there remains much room for improvement, particularly from the standpoint of high conversion, yield, and catalyst life. Other references of interest include U.S. Pat. Nos. 4,020,174; 4,094,816; 4,089,807; 3,296,282; 3,474,041 and British Patent No. 1,464,198. All of these references relate to catalyst regeneration and not to catalyst stability.

Also, U.S. Pat. Nos. 3,915,892 and 3,985,775 teach a process for preparing catalysts suitable for preparing maleic anhydride from n-butane comprising a mixed vanadium-phosphorus oxide wherein one of the process steps consists of heating the components to between 350° C. and 410° C. in an oxygen-containing gas. The function of this step is to remove water of hydration from the dihydrate of the mixed oxide of the vanadium and pentavalent phosphorus complex.

Our catalyst is suitably prepared in organic solvents by slurrying vanadium compounds and metals or metal oxides such as molybdenum oxide, zinc oxide, uranium oxide, tungsten oxide, tin oxide, bismuth oxide, titanium oxide, niobium oxide, antimony oxide and cobalt oxide in organic solvents, preferably organic ether solvents.

A small amount of water or a hydrogen donor compound, such as a lower alcohol, is also present in the ether. Suitable alcohols are aliphatic alcohols having from about 1 to about 8 carbon atoms. Preferred alcohols are ethanol and methanol. Suitable organic ether solvents are ethers having from about 2 to about 10 carbon atoms. Preferred ethers are tetrahydrofuran (THF), tetrahydropyran, 1,2-dimethoxyethane, bis(2-methoxyethyl)ether, 1,4 dioxane, ethylether, propylether, butylether, and pentylether. Phosphoryl halide is slowly added to the slurry. The water or hydrogen donor reacts with the phosphoryl halide to generate anhydrous phosphoric acid or phosphate esters and hydrogen halide gas. The hydrogen halide dissolves both the vanadium compound, for example, the vanadium pentoxide, and the co-metal compound and also reduces the vanadium from a valence state of about five to a valence state of about four. This reaction takes places at a temperature of about 0° C. to about 200° C.

While the reaction solution is being refluxed, if desired, a modifier or mixture of modifiers such as o-xylene, m-xylene, p-xylene, benzene, toluene, mesitylene, pseudocumene, phthalic anhydride, trimellitic anhydride, benzoic acid, toluic acid, phthalic acid, isophthalic acid, terephthalic acid, trimesic acid or trimellitic acid, is suitably added to the reaction solvent. After refluxing, the color of the solution is green. The volume of the solution is reduced by distillation or evaporation until it becomes a thick syrup. This syrup is dried at a temperature of about 130° C. to about 200° C. and 0–15 inches of mercury vacuum under an air purge. Once dry, the color of the solid material is brown. The catalyst can be formed into geometric forms, such as cylinders, using graphite, Sterotex or other lubricants such as stearic acid, zinc stearate or starch and binders such as polyvinyl alcohol. The catalyst in the form of geometric shapes or in powder form is suitably calcined in air or a nitrogen-air combination at a temperature of 300°–370° C. before loading into a suitable tubular reactor. The catalyst is activated further by the addition of water and phosphorus compounds or mixtures thereof such as alkylphosphates, phosphites, and phosphines. This activation takes place at a temperature of about 300° C. to about 500° C. Representative phosphorus compounds have the following structure:

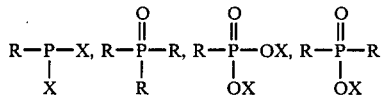

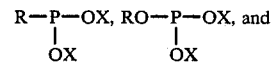

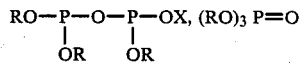

wherein R is phenyl or an alkyl radical of 1 to 6 carbon atoms and X is H or R. Suitable compounds are primary, $RPH_2$, secondary, $R_2PH$, and tertiary, $R_3P$, phosphines, such as ethyl phosphine; the tertiary phosphine oxides, $R_3PO$, such as tripropyl phosphine oxide, the primary, $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof, such as the monoethyl ester; the phosphinous acids, $R_2POX$, such as diethyl phosphinous acid and the esters thereof, such as the monoethyl ester; the primary, $ROP(OX)_2$, secondary, $(RO)_2POX$, and tertiary, $(RO)_3P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO)_3P=O$ wherein R is hydrogen or a $C_1$-$C_4$ alkyl, at least one R being a $C_1$-$C_4$ alkyl. The preferred phosphorus compounds are triethylphosphate and trimethylphosphate.

Our novel catalyst for the production of maleic anhydride comprising a phosphorus-vanadium mixed oxide or a phosphorus-vanadium-co-metal mixed oxide is heated at a temperature of about 650° F. to about 1300° in an inert atmosphere before being used as a catalyst for the production of maleic anhydride. The usual inert gas is nitrogen but helium and other inert gases can be utilized. It should be noted that if the catalyst is heated in air initially, catalysts are formed which will expand and in some instances may expand to the point of being crushed in a tubular reactor. These catalysts cannot be used in commercial operations requiring fixed bed reactors wherein the catalysts are charged into steel tubes because the pressure drop across the catalyst bed will be excessive.

The novel catalyst comprises a phosphorus-vanadium mixed oxide or a phosphorus-vanadium mixed oxide promoted by metals. The atomic ratio of the vanadium to phosphorus can suitable be in the range of 0.5:1 to 1.25:1.0. The total atomic ratio of vanadium to phosphorus advantageously is in the range of 0.75:1 to 1:1. It is preferred that the total atomic ratio of molybdenum, zinc, tungsten, uranium, tin, bismuth, titanium, niobium or cobalt to vanadium should be in the range of 0.001:1 to 0.2:1.

The co-metal, such as molybdenum, zinc, tungsten, uranium, bismuth, titanium, antimony, niobium, cobalt or tin may be added as a compound together with vanadium, or separately introduced into the solution. Suitable co-metal compounds comprise their oxides and soluble salts. Suitable molybdenum compounds comprise molybdenum oxide and most soluble molybdenum salts. If it is desired to improve physical properties of the catalysts, they may be treated with the suspension of an inert support, for example, alumina, titania, silicon carbide, kieselguhr, pumice or silica. The catalyst may be reinforced with such materials at any stage in its preparation.

According to our process, the average valence of vanadium is in the range of about 3.8 to 4.2. In our catalyst preparation, various phosphoryl halides may be used, but $POCl_3$ is preferred. The catalyst can be activated in the presence of water and:

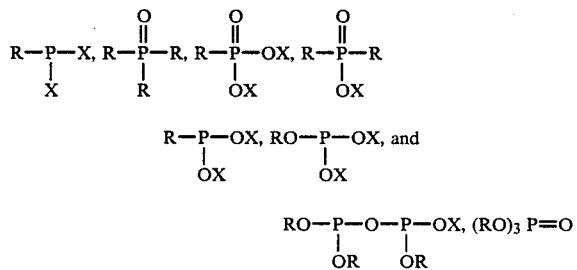

wherein R is phenyl or an alkyl radical of 1 to 6 carbon atoms and X is H or R. Suitable compounds are the primary, $RPH_2$, secondary, $R_2PH$, and tertiary, $R_3P$, phosphines, such as ethyl phosphine; the tertiary phosphine oxides, $R_3PO$, such as tripropyl phosphine oxide; the primary, $RP(O)(OX)_2$, and secondary, $R_2P(O)OX$, phosphonic acids, such as benzene phosphonic acid; the esters of the phosphonic acids, such as diethyl methanephosphonate; the phosphonous acids, $RPO_2X_2$, such as benzenephosphonous acid and the esters thereof such as the monoethyl ester; the phosphinous acids, $R_2POX$, such as diethyl phosphinous acid and the esters thereof, such as the monoethyl ester; the primary, $ROP(OX)_2$, secondary, $(RO)_2POX$, and tertiary, $(RO)_3P$, phosphites, such as diethyl phosphite, trimethyl phosphite, triethyl phosphite, triisopropyl phosphite, tripropyl phosphite and tributyl phosphite, and the pyrophosphites, such as tetraethyl pyrophosphite. The preferred phosphorus compound is an ester of orthophosphoric acid having the formula $(RO)_3P=O$ wherein R is hydrogen or a $C_1$-$C_4$ alkyl, at least one R being a $C_1$-$C_4$ alkyl. The preferred phosphate compounds are triethylphosphate and trimethylphosphate.

The amount of water added is about 1,000 to about 40,000 parts per million of the reaction feed gas stream. The reaction feed gas stream comprises hydrocarbon and air.

Suitable vanadium compounds include: vanadium oxides, such as vanadium pentoxide, vanadium trioxide and the like; vanadium oxyhalides, such as vanadyl chloride, vanadyl dichloride, vanadyl trichloride, vanadyl bromide, vanadyl dibromide, vanadyl tribromide and the like; vanadium-containing acids, such as metavanadic acid, pyrovanadic acid and the like; vanadium salts, such as ammonium meta-vanadate, vanadium sulfate, vanadium phosphate, vanadyl formate, vanadyl oxalate and the like; however, vanadium pentoxide is preferred.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen, but synthetic mixtures of oxygen and diluent gases, such as nitrogen also may be employed. Air enriched with oxygen may be used.

The gaseous feed stream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4,000 cc of feed per cc of catalyst per hour, and more preferably about 1,000 to 2,400 cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury at 0° C. A variety of reactors will be found to be useful, and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at relatively constant temperatures, and some medium to conduct heat from the reactors is necessary to aid temperature control. Such media may be Woods metal, molten sulfur, mercury, molten lead and the like, but it has been found that eutectic salt baths are completely satisfactory. One such salt bath is a sodium nitrate-sodium nitrite-potassium nitrate eutectic constant temperature mixture. An additional method of temperature control is to use a metal block reactor whereby the metal surrounding the tube acts as a temperature-regulating body. As will be recognized by one skilled in the art, the heat exchanger medium may be kept at the proper temperature by heat exchangers and the like. The reactor or reaction tubes may be iron, stainless steel, carbon steel, nickel, glass tubes such as vycor, and the like. Both carbon steel and nickel tubes have excellent long life under the conditions of the reaction described herein. Normally, the reactors contain a preheat zone under an inert material such as one-quarter-inch Alundum pellets, inert ceramic balls, nickel balls, or chips and the like present at about one-half to one-tenth the volume of the active catalyst present.

The temperature of reaction may be varied within some limits, but normally the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 20°–50° F. above the salt bath temperature. The temperature of the reactor, of course, will also depend to some extent upon the size of the reactor and the butane concentration.

The reaction may be conducted at atmospheric, superatmospheric, or subatmospheric pressure. The exit pressure will be at least slightly higher than the ambient pressure to ensure a positive flow from the reactor. The pressure of the inert gases must be sufficiently high to overcome the pressure drop through the reactor.

Maleic anhydride may be recovered by a number of ways well-known to those skilled in the art. For example, the recovery may be by direct condensation or by absorption in suitable media, with specific operations and purification of the maleic anhydride. The following examples will serve to provide full understanding of the invention, but it is to be understood that these examples are given for illustrative purposes only and will not be interpreted as limiting the invention in any way.

Maleic anhydride is currently produced by fixed bed catalytic oxidation of butane over mixed vanadium oxide catalyst. The catalyst is usually formed into tablets prior to loading in the multitubular reactor. The size and shape of these tablets are important since they determine the void fraction available in the reactor. It is important that this void fraction be large enough to avoid development of a large pressure drop across the reactor. One such suitable tablet is a right cylinder. In addition to its dependence on the shape and dimensions of the tablet, the reactor's void fraction depends on whether those dimensions change under hydrocarbon conversion conditions. For example if the tablet undergoes a volume increase or "expansion" the void fraction will decrease and an unacceptable increase in pressure drop will result.

We discovered that catalyst tablets may undergo undesirable expansion if they are heated at high temperatures in the presence of air or other oxygen containing gasses. Such conditions exist in our standard expansion test, which is described in more detail below, or in a pilot plant or commercial maleic anhydride reactor, particularly under reactor start-up conditions. The maleic anhydride catalysts may be subjected to temperatures in excess of 800° F. in the presence of air during these procedures and it is during this treatment that catalyst expansion occurs.

However, we have discovered, unexpectedly, that the undesirable catalyst expansion can be reduced greatly or eliminated entirely if the catalyst tablet or powder is first pre-treated at high temperatures in the presence of an inert or substantially inert atmosphere such as nitrogen or helium or other inert gas. The temperature for the pre-treatment of this invention is in the range of 650° to 1300° F., more preferably in the range of 700° to 900° F. After this pre-treatment the catalyst can be subjected to the conditions of the standard expansion test, or to pilot-plant or commercial reactor start-up or operating conditions, without undergoing undesirable catalyst expansion. It is necessary to conduct this catalyst pre-treatment in the inert atmosphere before the catalyst is exposed to air or other oxygen containing gas at high temperatures or else excessive catalyst expansion will occur.

Examples of the catalyst and process of this invention are provided as follows. It is to be understood that these examples are provided to illustrate some of the embodiments of this invention and are not intended to limit the scope of the invention.

TYPICAL CATALYST PREPARATION

To a 3-liter, 3-neck, round bottom flask equipped with a thermowell, electrical mantle, mechanical stirrer, and reflux condenser, were added 364 g $V_2O_5$, 17.28 g $MoO_3$, 270 g water, and 1,000 ml tetrahydrofuran (THF). $POCl_3$ (767 g) was added from an addition funnel over a period of 2 hours. During the $POCl_3$ addition an exothermic reaction occurs which results in a continuous temperature rise, reflux of the solvent and dissolution of the solids. The mixture turns from a yellow orange slurry to red brown solution as the $POCl_3$ addition progresses. At the end of $POCl_3$ addition the deep green solution is heated up to reflux and maintained at reflux for two hours. The deep green solution is then partially (500 ml) stripped of solvent. The thick black, green syrup is then dried overnight at about 3 in. of Hg vacuum with a mild air, nitrogen, or $N_2$/air purge passing through the oven. Drying temperature and time vary from 130° C. to 200° C. and 18 to 48 hours respectively.

The dark brown catalyst powder is ground, calcined at 300° C. in air for 4 hours and formed into 3/16" cylindrical tablets using 5 wt % graphite as a lubricant. The side crush strength of the tablets is about 5.9 lbs.

EXPANSION TEST

In an expansion test the length and diameter of 10 tablets are measured with a caliper. An average volume is determined using the volume relationship for a cylinder. The tablets are then introduced to an oven at 900° F. The tablets are kept at that temperature in a humid air stream for 2 hours. The tablets are removed from the oven and allowed to cool in a desiccator. The length and diameter of the tablets are measured and an average volume is determined. The comparison of the average volume of the tablet before and after introduction to the oven determines whether the tablets expanded, shrank, or remained the same.

EFFECT OF PRETREATMENT CONDITIONS ON TABLET VOLUME CHANGE: EXAMPLES 1-9

The effect of atmosphere and temperature on tablet volume change was determined in the following manner. The average volume of 60 tablets was determined by using the average length and diameter of all tablets and applying the volume relationship of a cylinder. These tablets (9.7 cc) were then loaded in a 0.62" diameter minireactor. After gas flow was established at a volume hourly space velocity (VHSV) of 1200 hr-1, the temperature was raised from ambient to target in about 30-45 minutes and held there for two hours. The reactor was then cooled and the tablets were removed. The volume of the tablets was then determined by using the average length and diameter of all pretreated tablets and applying the volume relationship for a cylinder. Tablet volume change of pretreated tablets was calculated relative to the volume of fresh tablets. The pretreatment atmosphere and temperature and tablet volume change are shown in Table I. The data clearly show that the inert atmosphere pretreatments result in larger tablet shrinkage than air pretreatments.

STANDARD TABLET EXPANSION TEST TO DETERMINE VOLUME CHANGES OF PRETREATED TABLETS: EXAMPLES 10-20

The invention is only useful if pretreated tablets do not expand further when subjected to a standard tablet expansion test. Our experience has been that tablet volume changes observed in such a test correlate well with tablet volume changes observed in pilot plant runs. The expansion test was carried out in the following manner. The average volume of 10 tablets from each of Examples 1-9 was determined. The tablets were then introduced into an oven, which was already set at 900° F., and kept there in a humid air stream for two hours. The tablets were then removed from the oven and allowed to cool in a desiccator. The length and diameter of the tablets were measured and the average volume was determined. This average volume was then compared with the volume of the fresh tablets prior to pretreatments described in Examples 1-9.

As shown in Table II, the air pretreated tablets underwent significant tablet expansion while tablet shrinkage was observed for tablets pretreated in $N_2$ and He at 800°-900° F. The inert atmosphere pretreatment at 700° F. appears to be less adequate than higher pretreatment temperatures since the tablets showed a positive volume change or expansion in the standard expansion test.

It appears then that a pretreatment temperature limit exists below which the invention is least preferred. In order to determine this limit we carried out two pretreatments in air and $N_2$ at 750° F. The pretreated tablets were then subjected to the same standard expansion test. The results are shown in Table III. The data show that the net volume change for the $N_2$ pretreated tablets is a desired shrinkage, while that of the air pretreated tablets is an undesired and significant expansion. Because of the small tablet volume change observed for the 750° F./$N_2$ pretreatments, the most preferred pretreatment temperature appears to be in the range of 700°-800° F.

BUTANE TO MALEIC ANHYDRIDE CONVERSION OF PRETREATED TABLETS

The catalytic performance of some of the pretreated tablets was determined in a minireactor test. A 6 cc charge of the pretreated tablets was loaded into a 0.62" diameter minireactor and evaluated with a feed of 1.1 mole % n-butane in synthetic air at a VHSV of 1200 hr-1. About 10,000 ppm of water were continually added to the reactor feedstream by passing it through a water saturator. The data are shown in Table IV.

The data show that, relative to air pretreatment, the inert atmosphere pretreatment at 800° F. did not result in a detrimental effect on catalytic performance. Furthermore, all catalysts exhibit very good selectivity and yield to maleic anhydride.

TABLE I

Tablet Volume Change as a Function[1] of Temperature and Atmosphere

| Example No. | Atmosphere | Temperature, °F. | Tablet Volume Change,[2] % |
|---|---|---|---|
| 1 | Air | 700 | +0.61 |
| 2 | | 800 | +2.18 |
| 3 | | 900 | +6.15 |
| 4 | $N_2$ | 700 | −5.04 |
| 5 | | 800 | −2.23 |
| 6 | | 900 | −2.56 |
| 7 | He | 700 | −4.82 |
| 8 | | 800 | −5.41 |
| 9 | | 900 | −3.33 |

Notes:
[1]In any experiment about 9.7 cc of tablets (60 tablets) were subjected to gas flow (VHSV = 1200 hr-1) at the indicated temperature for two hours.
[2]Tablet volume change is relative to the volume of fresh tablets.

TABLE II

Net Tablet Volume Change of Pretreated Tablets[1] as a Result of a Standard Tablet Expansion Test

| Example No. | Pretreatment | Tablet Volume Change,[2] % |
|---|---|---|
| 10 | Air, 700° F. | +8.10 |
| 11 | Air, 800° F. | +10.19 |
| 12 | Air, 900° F. | +9.46 |
| 13 | $N_2$, 700° F. | +3.3 |
| 14 | $N_2$, 800° F. | −2.36 |
| 15 | $N_2$, 900° F. | −3.93 |
| 16 | He, 700° F. | +8.04 |
| 17 | He, 800° F. | −3.93 |
| 18 | He, 900° F. | −4.24 |

Notes:
[1]Tablet volume change was obtained in a standard tablet expansion test.
[2]Tablet volume change is the net change relative to volume of fresh tablets prior to treatment.

TABLE III

Net Volume Change of Pretreated Tablets as a Result of a Standard Tablet Expansion Test

| Example No. | Pretreatment | Tablet Volume Change[1] |
|---|---|---|
| 19 | $N_2$, 750° F. | −0.19 |
| 20 | Air, 750° F. | +8.7 |

Note:
[1]Tablet volume change is the net change relative to volume of fresh tablets prior to pretreatment.

TABLE IV

Butane Conversion to Maleic Anhydride Performance of Pretreated Catalysts

| Catalyst from Example | 2 | 5 | 8 |
|---|---|---|---|
| Pretreatment Atmosphere | Air | $N_2$ | He |
| Pretreatment Temperature, °F. | 800 | 800 | 800 |
| Hours on Stream | 192 | 192 | 192 |
| Temperature, °F. | 791 | 791 | 789 |
| Conversion, Mole %[1] | 84 | 83 | 82 |

TABLE IV-continued

Butane Conversion to Maleic Anhydride Performance of Pretreated Catalysts

| Catalyst from Example | 2 | 5 | 8 |
|---|---|---|---|
| Selectivity, Mole %[2] | 64 | 64 | 64 |

Note:
[1]Conversion, % = $\frac{\text{moles n-butane reacted}}{\text{moles n-butane in feed}} \times 100$

[2]Selectivity, % = $\frac{\text{moles maleic anhydride produced}}{\text{moles n-butane consumed}} \times 100$

We claim:

1. A catalyst for the production of maleic anhydride by the oxidation of a member of the group consisting of benzene, butane, butene and butadiene, which catalyst comprises a phosphorus-vanadium-mixed oxide and exists in the form of geometric shapes, said shapes having been heated in an inert atmosphere at a temperature of about 650° to about 1300° F. prior to being exposed to an oxygen-containing gas at an elevated temperature.

2. The catalyst of claim 1 wherein a co-metal is used as a promoter, the total ratio of the co-metal to vanadium being in the range of about 0.001:1 to about 0.2:1.

3. The catalyst of claim 2 wherein the co-metal is molybdenum.

4. The catalyst of claim 2 wherein the co-metal is zinc.

5. The catalyst of claim 1 wherein the catalyst is heated in an inert atmosphere at a temperature of about 700° to about 900° F.

6. A process for the manufacture of a phosphorus-vanadium oxide catalyst suitable for use in the manufacture of maleic anhydride from butane or other hydrocarbon feedstock, which process comprises reacting at a temperature of about 0° C. to about 200° C. a vanadium compound in an organic ether solvent having from about 2 to about 10 carbon atoms with a phosphoryl halide in the presence of water or an aliphatic alcohol having from about 1 to about 8 carbon atoms to form a reaction solution, forming a thick syrup from said reaction solution, drying said syrup to form a solid material, grinding said solid material to form a powder, calcining said powder in an oxygen-containing gas to provide a calcined powder, forming said calcined powder into geometric shapes, and heating said geometric shapes at a temperature of about 650° to about 1300° F. in an inert atmosphere prior to said geometric shapes being exposed to an oxygen-containing gas at an elevated temperature.

7. The process of claim 6 wherein the vanadium compound is vanadium pentoxide.

8. The process of claim 6 wherein said organic ether solvent is tetrahydrofuran.

9. The process of claim 6 wherein said geometric shapes are heated at a temperature of about 700° to about 900° F. in an inert atmosphere.

10. A process for the manufacture of a phosphorus-vanadium co-metal oxide catalyst suitable for use in the manufacture of maleic anhydride from butane or other hydrocarbon feedstocks, which process comprises reacting at a temperature of about 0° C. to about 200° a vanadium compound in an organic ether solvent having from about 2 to about 10 carbon atoms with a phosphoryl halide in the presence of water or an aliphatic alcohol having from about 1 to about 8 carbon atoms to form a reaction solution, forming a thick syrup from said reaction solution, drying said syrup to form a solid powdery material, optionally calcining said powdery material in air, forming said powdery material into geometric shapes, and heating said geometric shapes at a temperature of about 650° to about 1300° F. in an inert atmosphere prior to said geometric shapes being exposed to an oxygen-containing gas at an elevated temperature.

11. The process of claim 10 wherein the co-metal is molybdenum.

12. The process of claim 10 wherein the co-metal is zinc.

13. The process of claim 11 wherein the vanadium compound is vanadium pentoxide.

14. The process of claim 12 wherein the vanadium compound is vanadium pentoxide.

15. The process of claim 11 wherein the organic ether solvent is tetrahydrofuran.

16. The process of claim 12 wherein the organic ether solvent is tetrahydrofuran.

17. The catalyst of claim 1, said catalyst having been activated by treatment in the presence of water with a phosphorus compound selected from the group consisting of:

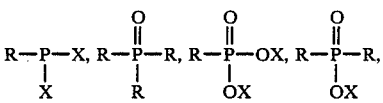

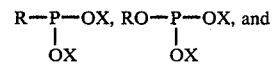

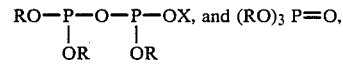

wherein R is phenyl or an alkyl radical of 1 to 6 carbon atoms and X is H or R.

18. The catalyst of claim 1 wherein said geometric shapes comprise tablets.

19. The catalyst of claim 2 wherein said geometric shapes comprise tablets.

20. The process of claim 6 wherein the geometric shapes of said catalyst comprise tablets.

21. The process of claim 10 wherein the geometric shapes of said catalyst comprise tablets.

22. The catalyst of claim 17 wherein said phosphorus compound is the alklylester of orthophosphoric acid having the structure $(RO)_3P=O$, wherein R is hydrogen or a $C_1$ to $C_4$ alkyl, at least one R being a $C_1$ to $C_4$ alkyl.

23. The catalyst of claim 22 wherein said alkylester is triethylphosphate.

24. The catalyst of claim 22 wherein said alkylester is trimethylphosphate.

* * * * *

UNITED STATES PATENT OFFICE
CERTIFICATE OF CORRECTION

Patent No. 4,933,312               Dated June 12, 1990

Inventor(s) Muin S. Haddad and Bernard L. Meyers and William S. Eryman

It is certified that error appears in the above-identified patent and that said Letters Patent is hereby corrected as shown below:

| Col. | Line | |
|------|------|---|
| 3 | 24 | "suitable" should read --suitably-- |

Signed and Sealed this

Fourteenth Day of January, 1992

Attest:

HARRY F. MANBECK, JR.

Attesting Officer

Commissioner of Patents and Trademarks